US011400230B2

(12) United States Patent
Klemm (10) Patent No.: US 11,400,230 B2
(45) Date of Patent: Aug. 2, 2022

(54) READING DEVICE, DRUG DELIVERY DEVICE AND DRUG DELIVERY DEVICE IN COMBINATION WITH A READING DEVICE

(71) Applicant: Sanofi-Aventis Deutschland GMBH, Frankfurt am Main (DE)

(72) Inventor: Thomas Klemm, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 416 days.

(21) Appl. No.: 16/330,259

(22) PCT Filed: Sep. 8, 2017

(86) PCT No.: PCT/EP2017/072578
§ 371 (c)(1),
(2) Date: Mar. 4, 2019

(87) PCT Pub. No.: WO2018/046660
PCT Pub. Date: Mar. 15, 2018

(65) Prior Publication Data
US 2019/0184110 A1    Jun. 20, 2019

(30) Foreign Application Priority Data

Sep. 9, 2016  (EP) .................................. 16188184

(51) Int. Cl.
*A61M 5/31* (2006.01)
*A61M 5/315* (2006.01)
*A61M 5/24* (2006.01)

(52) U.S. Cl.
CPC .......... *A61M 5/31568* (2013.01); *A61M 5/24* (2013.01); *A61M 5/31551* (2013.01);
(Continued)

(58) Field of Classification Search
CPC .. A61M 2005/3126; A61M 2205/3306; A61M 2205/3317; A61M 2205/3561;
(Continued)

(56) References Cited

U.S. PATENT DOCUMENTS 6,221,051 B1 * 4/2001 Hjertman .............. A61M 5/145
604/189
9,764,095 B2 * 9/2017 Draper .................... A61M 5/20
(Continued)

FOREIGN PATENT DOCUMENTS

CN          1671432        9/2005
CN          103648555      3/2014
(Continued)

OTHER PUBLICATIONS

PCT International Preliminary Report on Patentability in International Appln. No. PCT/EP2017/072578, dated Mar. 12, 2019, 8 pages.
(Continued)

*Primary Examiner* — William R Carpenter
(74) *Attorney, Agent, or Firm* — Fish & Richardson P.C.

(57) ABSTRACT

The present disclosure provides a reading device adapted to read-out infrared readable data provided by a covered part of a movable component of a drug delivery device, wherein the reading device comprises at least one electromagnetic radiation source configured to emit infrared radiation and adapted to illuminate the infrared readable data on the covered part; at least one optical sensor unit configured to detect infrared radiation reflected from the covered part of the movable component; and at least one processing unit configured to determine a data value of the infrared readable data as a function of the detected reflected infrared radiation. The disclosure further provides a drug delivery device and a drug delivery device in combination with the reading device.

13 Claims, 5 Drawing Sheets

(52) U.S. Cl.
CPC ............. *A61M 2005/3126* (2013.01); *A61M 2205/3306* (2013.01); *A61M 2205/3317* (2013.01); *A61M 2205/3561* (2013.01); *A61M 2205/502* (2013.01); *A61M 2205/52* (2013.01); *A61M 2205/587* (2013.01)

(58) Field of Classification Search
CPC ........ A61M 2205/502; A61M 2205/52; A61M 2205/587; A61M 5/24; A61M 5/31551; A61M 5/31568
See application file for complete search history.

(56) References Cited

U.S. PATENT DOCUMENTS

| | | |
|---|---|---|
| 2008/0287865 A1 | 11/2008 | Nielsen et al. |
| 2013/0310756 A1* | 11/2013 | Whalley ............ A61M 5/3129 604/189 |
| 2014/0018768 A1 | 1/2014 | Hayes et al. |
| 2016/0051766 A1* | 2/2016 | Marsh ................ A61M 5/3157 604/207 |
| 2016/0051770 A1* | 2/2016 | Jones ............... A61M 5/31553 604/211 |

FOREIGN PATENT DOCUMENTS

| | | |
|---|---|---|
| CN | 103957961 | 7/2014 |
| CN | 104411349 | 3/2015 |
| EP | 3045186 | 7/2016 |
| JP | 2007-278927 | 10/2007 |
| JP | 2015-518747 | 7/2015 |
| JP | 2016-502899 | 2/2016 |
| JP | 2016-512966 | 5/2016 |
| WO | WO 2004/009163 | 1/2004 |
| WO | WO 2013/004843 | 1/2013 |
| WO | WO 2013/050535 | 4/2013 |
| WO | WO 2013/177135 | 11/2013 |
| WO | WO 2014/111340 | 7/2014 |
| WO | WO 2014/111341 | 7/2014 |
| WO | WO 2015/185686 | 12/2015 |
| WO | WO 2015/189173 | 12/2015 |
| WO | WO 2016/055400 | 4/2016 |
| WO | WO 2016/100055 | 6/2016 |
| WO | WO 2016/116566 | 7/2016 |

OTHER PUBLICATIONS

PCT International Search Report and Written Opinion in International Appln. No. PCT/EP2017/072578, dated Nov. 24, 2017, 11 pages.

* cited by examiner

READING DEVICE, DRUG DELIVERY DEVICE AND DRUG DELIVERY DEVICE IN COMBINATION WITH A READING DEVICE

CROSS REFERENCE TO RELATED APPLICATIONS

The present application is the national stage entry of International Patent Application No. PCT/EP2017/072578, filed on Sep. 8, 2017, and claims priority to Application No. EP 16188184.2, filed on Sep. 9, 2016, the entire disclosures of which are incorporated herein by reference.

TECHNICAL FIELD

This disclosure generally relates to a reading device. The disclosure further relates to a drug delivery device and to a drug delivery device in combination with a reading device.

BACKGROUND

Administering an injection is a process which presents a number of risks and challenges for users and healthcare professionals, both mental and physical. Such injections can be performed by using injection devices, which are applied either by medical personnel or by patients themselves.

SUMMARY

Pen type drug delivery devices and autoinjectors have been designed and developed to perform regular injections by persons without formal medical training. This is increasingly common among patients having diabetes where self-treatment enables such patients to conduct effective management of their disease. For example, an insulin dose needed to be injected can be manually selected by turning a dosage knob arranged on a pen device and observing the actual dose from an aperture or dose window of the pen device. The dose is then injected by inserting the needle into a suited skin portion and pressing an injection button of the pen device. To be able to monitor the insulin injection, in particular to prevent false handling of the pen device or the autoinjector or to keep track of the doses that are already applied, it is desirable to measure information related to a condition and/or use of a drug delivery device, such as a selected dose.

Described herein is an improved reading device, an improved drug delivery device and a drug delivery device in combination with such a reading device.

A reading device, a drug delivery device, and a drug delivery device in combination with a reading device are described in the claims. Exemplary embodiments are provided in the dependent claims.

BRIEF DESCRIPTION OF THE DRAWINGS

The present disclosure will become more fully understood from the detailed description given below and the accompanying drawings, which are given by way of illustration only, and do not limit the present disclosure.

Corresponding parts are marked with the same reference symbols in all figures.

DETAILED DESCRIPTION

The disclosure relates to a reading device that is adapted to read-out infrared readable data that is provided on a movable component of a drug delivery device. The reading device comprises at least one electromagnetic radiation source configured to illuminate a covered part of the movable component, at least one optical sensor unit configured to emit infrared radiation and adapted to detect infrared radiation reflected from the covered part of the movable component and at least one processing unit that is configured to determine a value as a function of the detected reflected infrared radiation.

The reading device allows measuring information related to a condition and/or use of a drug delivery device, such as a selected dose. For instance, a patient having diabetes needs to select a specific dose of insulin required for achieving a good blood glucose level. A patient performing self-administration of insulin will commonly need to select a dose of insulin between 1 and 80 International Units. The provided reading device allows reading out infrared readable data invisible to a user without the requirement of an additional window or aperture in the drug delivery device. Furthermore, the reading device enables indicating a selected dose as well as recording dosage history. The dosage history may be an important factor in calculating future doses.

The reading device may optionally comprise a transmitter to transmit the data and/or the data value as read from the drug delivery device to another device, e.g. transmit the data wirelessly, for example via radio or Bluetooth® connection, to a mobile phone or a walk-by device or a remote terminal.

According to a further embodiment the reading device is configured as an integral component of the drug delivery device. Alternatively the reading device may be supplemental to the drug delivery device. For example, the reading device may be configured to be attached to the drug delivery device, for example releasably or alternatively irreleasably.

In particular, the at least one electromagnetic radiation source may be configured as a light emitting diode (LED) emitting infrared radiation. Infrared radiation emitting diodes are powerful, economical and durable components at least until a wavelength range of 900 nm. Furthermore, emitting infrared radiation allows transmitting through the opaque part of the case of the drug delivery device and thus reading out the infrared readable data that is covered by the case and/or by additional layers applied onto the movable component.

To improve the signal quality, the at least one electromagnetic radiation source may be coupled to a power source configured to supply pulsed electric current. In particular, the power source is configured to supply a pulsed electric current high enough for the at least one electromagnetic radiation source to emit infrared radiation with an intensity significantly higher than extraneous light. This enables an easy evaluation of the measured electromagnetic radiation by the processing unit, e.g., by using tresholding. For evaluation, the processing unit may be alternatively or additionally coupled to or provided with a pulse width modulation generator or with a pseudo-random signal generator.

For detecting electromagnetic radiation, in particular infrared radiation, emitted by the at least one electromagnetic radiation source and reflected from a surface of the movable component, the reading device comprises the at least one optical sensor unit, which may comprise a number of photodiodes, e. g. silicon photodiodes, for detection. Alternatively, the at least one optical sensor unit may comprise an optical waveguide. The reading device may further comprise a processing unit for analysing the signals of the optical sensor unit.

The analysis could provide a decoding of an encoded infrared readable signal or a signal strength interpretation.

In an exemplary embodiment, the at least one electromagnetic radiation source is arranged adjacent to the at least one optical sensor unit such that the at least one optical sensor unit is capable to detect infrared radiation that is emitted by the at least one electromagnetic radiation source and reflected by the covered and invisible part of the movable component.

In an exemplary embodiment, the at least one optical sensor unit comprises a number of photodiodes, wherein the at least one electromagnetic radiation source is arranged adjacent to the number of photodiodes. In particular, the at least one electromagnetic radiation source may be arranged horizontally side-by-side having a small distance to each other so that the number of photodiodes detects only reflected infrared radiation and not directly emitted infrared radiation. The adjacent arrangement enables the detection of a high proportion of the reflected infrared light.

In an exemplary embodiment, the optical sensor unit may comprise an array of a plurality of photodiodes forming an image sensor that is adapted for high speed parallel read out. In particular, the optical sensor unit must be capable of providing sufficient resolution in order to enable reading out the infrared readable data, in particular encoded infrared readable data provided on the movable component. For example, the infrared readable data uses an 8-bit array and the optical sensor unit comprises an array of about 20-80 photodiodes. This number of photodiodes is capable to provide sufficient resolution in order to enable reading the 8-bit code information and to allow the processor unit to decode the encoded infrared readable data. The array of photodiodes may be assigned to one single electromagnetic radiation source.

In an alternative exemplary embodiment, the optical sensor unit may comprise a one-dimensional array of a few photodiodes, e.g., six photodiodes adjacent to each other, forming a simple light sensitive sensor. Every single photodiode may be assigned to one electromagnetic radiation source for detecting if an electromagnet radiation signal is detected or not. This configuration of the optical sensor unit may be suitable for detecting an axial position of a gauge element of the drug delivery device which is adapted to cover a part of a window arranged within the case through which a currently set or remaining dose of medicament is indicated.

A semiconductor material used for the photodiode depends on the spectral sensitivity of the required wavelength range. For example, silicon may be used to produce the photodiode or photodiodes. Such silicon photodiodes are cost-effective and comprise peak sensitivity at a wavelength range of 905 nm, which is close to a peak wavelength emission spectrum of the infrared light emitting diode.

Furthermore, the processing unit may be configured to determine a position of the movable component relative to a case of the drug delivery device. The determined relative position of the movable component enables determining a currently selected dose of medicament contained within the drug delivery device. For indicating the value determined by the processing unit, the reading device further comprises a display. The reading device may also comprise a memory unit for storing history data, whereby the history data comprises at least information about dose size, injection time, injection duration and drug type.

The disclosure further relates to a drug delivery device adapted to dispense a variable dose of a medicament and to couple to a reading device according to the disclosure, wherein the drug delivery device comprises a case and a movable component, wherein the movable component is arranged within the case and wherein the movable component is movable with respect to the case.

The movable component is provided with infrared readable data that is assigned to visual data. The infrared readable data is represented by a number of at least one of infrared readable symbols, signs, characters, icons, markings, codes, bars and signals.

The visual data is represented by a sequence of at least one of visual symbols, signs, characters, icons, markings, codes, bars and signals, whereby the number of infrared readable data is assigned to the sequence of visual data and each visual data indicates a dose of medicament.

The number of infrared readable data is arranged on a covered part of the movable component that is opaque to visible light.

The drug delivery device provides the visual data, in particular encoded visual data for visibly indicating a selected or remaining dose of medicament wherein the infrared readable data are assigned to the sequence of visual data. The visual data can be read out by the reading device and may be indicated as a selected or remaining dose of medicament by a displayed value. Due to the covered and invisible arrangement of the infrared readable data, the drug delivery device can be operated without any visible interference for the user.

Furthermore, the infrared readable data and the visual data are assigned to the same data value characterizing at least one of a parameter, a state, a dose and a position of at least one of a medicament, a component of the drug delivery device and the drug delivery device.

In an exemplary embodiment, the number of machine or infrared readable symbols may be represented as a number of metal areas printed on a surface of the covered part of the movable component. The infrared radiation transmitted through the case will be reflected when striking the metal area due to suppression of wave propagation beyond the so-called skin depth of metal. That means metal provides high contrast with remaining plastic parts of the drug delivery device when using an infrared light emitting diode as the electromagnetic radiation source. As a result, a signal-to-noise ratio may be substantially high. Here, the sequence of visual data, e.g. symbols may be arranged on a visible part of the movable component or on a dose indicator sleeve that is partly visible through a window, e. g. an aperture that is arranged within the case such that at least the visual symbol is visible through the window, which represents the currently selected dose of medicament.

The drug delivery device may be configured such that the covered part of the movable component is covered by an opaque part of the case and/or by an opaque outer surface of the movable component. Here, the infrared radiation is allowed to be transmitted through the opaque part of the case and/or through the opaque outer surface of the movable component in order to illuminate the covered and invisible part of the movable component on which the machine readable symbols, in particular the infrared readable symbols are arranged. This configuration enables the user to visibly indicate the selected or remaining dose of medicament and at the same time enabling another indication of the selected or remaining dose of medicament, e.g., by digital indication, without requiring an additional window or aperture.

In an exemplary embodiment, the infrared readable data is represented by a plurality of infrared readable symbols or the like, wherein each of the infrared readable data is assigned to one of the visual data respectively. For example, every visual symbol printed on the movable component is represented by an infrared readable symbol. One infrared readable data may be configured as a binary code. For this case, the optical sensor unit may be configured as an image sensor.

The infrared readable data may be applied onto the covered part of the movable component respectively, wherein the covered part may be an inner surface that is covered by the visible part of the movable component, which is configured as an opaque layer of white colour or plastic.

Furthermore, the visual data are arranged onto the visible part of the movable component, wherein the machine readable data, in particular infrared readable data are arranged onto the covered part of the movable component in a manner that each visual data that is currently visible through the window and the machine or infrared readable data assigned to this visual data are arranged phase-shifted to each other on the movable component. Thus a read-out point of the machine or infrared readable data is phase-shifted to the visual data currently visible through the window. That means, the machine or infrared readable data, e.g., a symbol and the visual data, e.g., a symbol that is currently visible through the window are offset to each other at a determined angle in a plane that is perpendicular to a longitudinal axis of the drug delivery device.

Alternatively, the infrared readable data is represented by a single metal area arranged on the covered part of the movable component, whereby the covered part may be configured as an outer surface that is arranged adjacent a gauge window. The gauge window is arranged within the movable component. The visual data is represented for example by a sequence of numbers arranged on a dose indicator sleeve, whereby the dose indicator sleeve is rotatable with respect to the case and with respect to the movable component.

Here, the movable component is configured as a sleeve-like component that is arranged between the case and the dose indicator sleeve, whereby the movable component is axially movable with respect to the case and interacts mechanically with a piston. The piston is arranged within a medicament container in a manner that the visual data, e.g. a symbol indicated through the window and/or the gauge window will be ejected from the medicament container. The gauge window is arranged with respect to the window of the case such that at least a part of the dose indicator sleeve is visible through the window and the gauge window. The position of the gauge window may thus be used to identify the currently set and/or dispensed dose of medicament.

A drug delivery device in combination with a reading device may comprise a case and a movable component, whereby the movable component is arranged within the case. The movable component is furthermore movable with respect to the case and is provided with infrared readable data that is assigned to visual data. The reading device is adapted to read-out the infrared readable data.

The reading device comprises at least one electromagnetic radiation source that is configured to emit electromagnetic radiation and that is adapted to illuminate the covered part of the movable component. The reading device further comprises at least one optical sensor unit that is configured to detect electromagnetic radiation reflected from the movable component. Moreover, the reading device comprises at least one processing unit that is configured to determine a value as a function of the measured reflected electromagnetic radiation.

The combination of the drug delivery device and the reading device allows detecting information related to a state, condition, parameter, dose and/or use of the drug delivery device, such as a selected dose without the requirement of an additional window or aperture in the case of the drug delivery device.

In particular, the at least one electromagnetic radiation source may be configured to emit infrared radiation which is allowed to transmit through a plastic material, which is conventionally used for the case of the drug delivery device.

Further scope of applicability of the present disclosure will become apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

Figure 1:
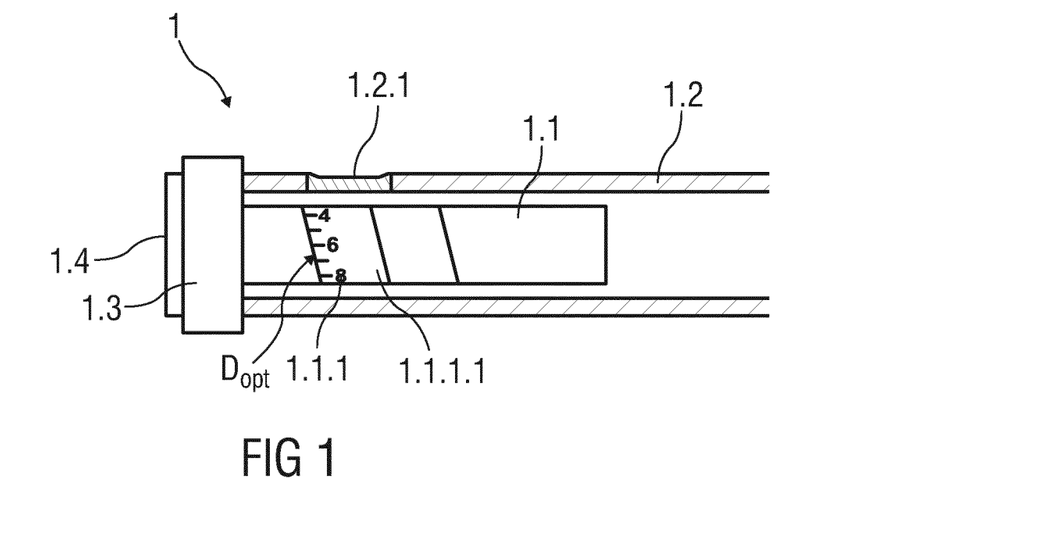
FIG. 1 is a schematic section of a cut-out of an exemplary embodiment of a drug delivery device comprising a movable component, according to the embodiments of the present disclosure.

FIG. 1 schematically shows a cut-out of a longitudinal section of an exemplary embodiment of a drug delivery device 1 comprising a movable component 1.1.

The drug delivery device 1 may be configured as a pre-filled, disposable injection pen or as an autoinjector comprising a case 1.2 receiving the movable component 1.1 and at least a medicament container 1.5 (see FIG. 10) to which a needle may be fixed (not illustrated). The needle may be protected by an inner needle cap and an outer needle cap (not illustrated).

A dose of medicament to be ejected from the drug delivery device 1 can be selected by turning a dose selector 1.3, e. g. a dial grip, in a rotational direction and the selected dose is then displayed through an window 1.2.1 arranged within the case 1.2. The selected dose may be indicated by a sequence of visual symbols 1.1.1 that represents visual data $D_{ow}$. The visual symbols 1.1.1 are arranged on a visible part 1.1.1.1 of the movable component 1.1, whereby the visible part 1.1.1.1 is an outer circumference. Hence, the sequence of visual symbols 1.1.1 may be printed or laser marked spirally around the outer circumference of the movable component 1.1. The visual symbols 1.1.1 may be further printed as numbers, icons, bars or the like. In an exemplary embodiment, the visual symbols 1.1.1 may represent values of so-called International Units (IU), whereby one IU may be a value of 0.0347 mg of human insulin. The window 1.2.1 is a transparent part of the case 1.2 permeable for visible light and may have dimensions enabling indicating exactly one visual symbol 1.1.1. For example, the window 1.2.1 is configured as an aperture.

The movable component 1.1 may be configured as a sleeve-like component forming a number sleeve movable with respect to the case 2 and mechanically interacting with a piston 1.6 (see FIG. 10) in the medicament container 1.5 in a manner that, when the needle is pierced into a suited skin portion of a patient and a button 1.4 is pushed, the visual symbol 1.1.1 that is indicated through the window 1.2.1 and that corresponds with the selected dose of medicament will be ejected from the drug delivery device 1. Here, the movable component 1.1 is caused to rotate and to move axially relative to the case 1.2 when an amount of medicament is selected or ejected. The visual symbols 1.1.1 printed on the movable component 1.1 successively align with the window 1.2.1 as the movable component 1.1 moves rotationally and axially. When an amount of medicament has been selected, the visual symbol 1.1.1 corresponding to the dialled amount of medicament is visible through the window 1.2.1. When the medicament is dispensed, a rotational and axial movement of the movable component 1.1 cause the visual symbol 1.1.1, which is currently visible through the window 1.2.1, to be that associated with the selected amount of medicament remaining in the drug delivery device 1 yet to be dispensed.

The case 1.2 of the drug delivery device 1 may comprise support elements (not illustrated), e.g., one or more protrusions and/or one or more indentations, which allow releasably attaching a reading device 2 adapted to read out infrared readable data D associated to the selected or remaining amount of medicament.

Figure 2:
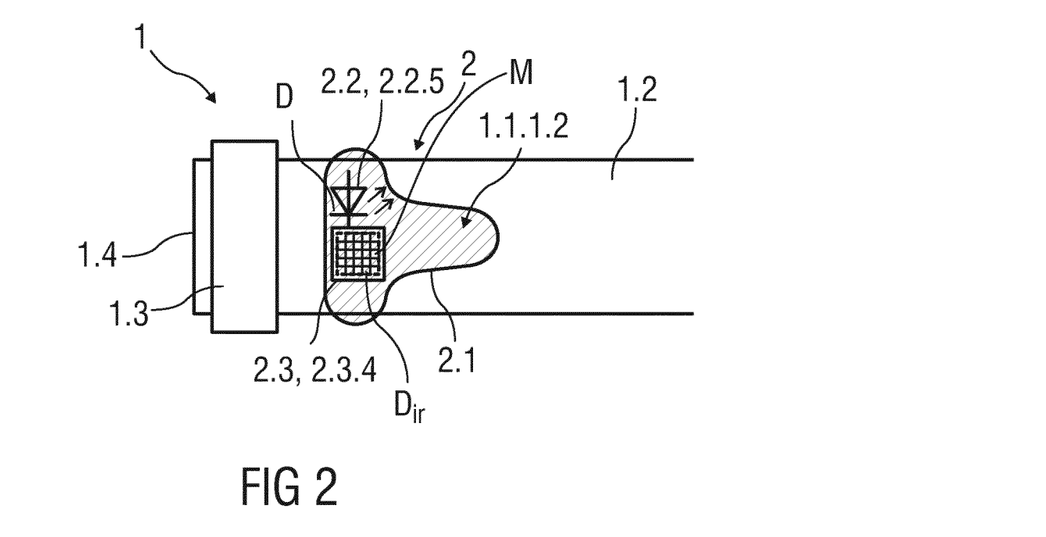
FIG. 2 is a schematic perspective view of a cut-out of an exemplary embodiment of a drug delivery device and a reading device comprising an electromagnetic radiation source and an optical sensor unit, according to the embodiments of the present disclosure.

FIG. 2 shows a perspective view of an exemplary embodiment of a reading device 2 attached to the drug delivery device 1.

The reading device 2 is configured as an integral component of the drug delivery device 1. The reading device 2 comprises a housing 2.1, which receives at least one electromagnetic radiation source 2.2 and at least one optical sensor unit 2.3. Alternatively, the at least one electromagnetic radiation source 2.2 and at least one optical sensor unit 2.3 may be arranged on an outside of the housing 2.1.

Figure 8:
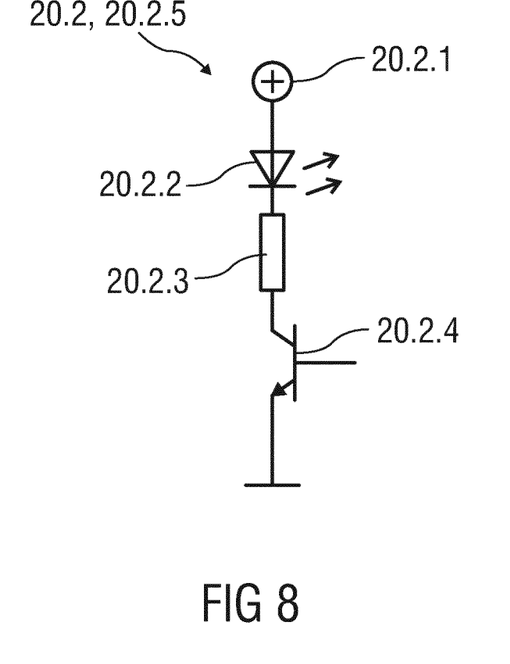
FIG. 8 is a circuit diagram of an electromagnetic radiation source of a reading device, according to the embodiments of the present disclosure.

The electromagnetic radiation source 2.2 may be configured as a light emitting diode emitting infrared radiation (see FIG. 8). Infrared radiation emitting diodes are known as providing maximum intensity at a wavelength of around 900 nm.

Common materials used for the case 1.2, e.g., polypropylene, have a high transmissivity for infrared radiation but are opaque to visible light such that a user cannot view through the case. Thus, the emitted infrared radiation is allowed to be transmitted through the opaque case 1.2 until hitting a reflecting component. According to the disclosure, the reflecting component is the infrared readable data D and is provided on a covered part 1.1.1.2 part of the movable component 1.1, which is arranged within the case 1.2. The infrared readable data D is represented by infrared readable symbols $D_{ir}$. The infrared readable symbols $D_{ir}$ may be configured as a metal part, e.g., a two-dimensional metal area M representing a binary code, whereby every visual symbol 1.1.1 is dedicated to one infrared readable symbols $D_{ir}$. Alternatively, the two-dimensional binary code is configured as a one dimensional binary code, e.g., a bar code. Further alternatively, the infrared readable data D may be represented by at least one of infrared readable signs, characters, icons and markings. The signs, characters, icons or markings may be optionally encoded.

Because the infrared readable symbols $D_{ir}$ are configured as a metallized parts, the part of the movable component 1.1, on which the infrared readable symbols $D_{ir}$ are arranged, provides high contrast with remaining plastic parts of the drug delivery device 1 when using an infrared radiation emitting diode as the electromagnetic radiation source 2.2.

The infrared readable data D, in particular the symbols $D_{ir}$ may be printed onto the covered part 1.1.1.2 of the movable component 1.1 that may be configured as an inner surface of an outer wall of the movable component 1.1. For being invisible to a user viewing through the window 1.2.1 and thus be invisible for a transparent or light permeable part of the case 1.2, the infrared readable symbols $D_{ir}$ may be covered by the visible part 1.1.1.1 of the movable component 1.1 that is configured as a thin layer of plastic or colour. For example, every visual symbol 1.1.1 is printed onto a thin layer provided on the outer wall of the movable component 1.1, whereby the respective infrared readable symbol $D_{ir}$ is provided below this layer regarding a radial inward direction and being thus invisible for a user.

The drug delivery device 1 may provide 120 doses of medicament to be ejected from the drug delivery device 1. That corresponds to a coding of 6.9 bits and thus approximately 7 bits and as a result a code element is required to comprise eight pixels at minimum (see FIG. 3). Due to the orderly sequence of the visual symbols 1.1.1, here printed as numbers, only the even numbers may be printed onto the movable component 1.1. This enables decreasing the coding to 5.9 bits or approximately 6 bits, respectively. Codes those are difficult to detect, such as all pixels are filled or empty, may be omitted.

The optical sensor unit 2.3 is adapted to receive electromagnetic radiation that is reflected when striking the metallized infrared readable symbols $D_{ir}$ due to a suppression of wave propagation beyond the so-called skin depth of metal. In particular, metal provides high contrast with remaining plastic parts of the drug delivery device 1 when using an infrared radiation emitting diode as the electromagnetic radiation source 2.2. As a result a signal-to-noise ratio (SNR) may be substantially high. Due to the binary code configuration of the infrared readable data D, the optical sensor unit 2.3 preferably comprises an array of a plurality of photodiodes 2.3.4 forming an image sensor that measures the intensity of the electromagnetic radiation reflected from the binary code (see FIG. 6).

The electromagnetic radiation source 2.2 and the optical sensor unit 2.3 are arranged adjacent to each other on the outside of the housing 2.1 facing the outer circumference of the case 1.2 of the drug delivery device 1. In particular, the electromagnetic radiation source 2.2 and the optical sensor unit 2.3 are arranged horizontally side-by-side with a small distance to each other such that the optical sensor unit 2.3 is capable to detect electromagnetic radiation that is emitted by the electromagnetic radiation source 2.2 and reflected from the covered part 1.1.1.2. The optical sensor unit 2.3 may be optically isolated from the electromagnetic radiation source 2.2 to avoid detecting (unreflected) electromagnetic radiation directly from the electromagnetic radiation source 2.2. This may be realized by a milling groove or a metal layer between the electromagnetic radiation source 2.2 and the optical sensor unit 2.3. Furthermore, the electromagnetic radiation source 2.2 and/or the optical sensor unit 2.3 may be provided with or coupled to a number of optical elements, e.g. optical lenses, for optimizing a directive efficiency of the emitted electromagnetic radiation and/or reflected electromagnetic radiation. Due to the fact that the drug delivery device 1 may comprise other metal components or parts, the reading device 2 and the drug delivery device 1 are required to be arranged to each other in a manner enabling substantially direct contact between the reading device 2 and the drug delivery device 1.

The combination of an infrared radiation emitting diode 2.2.5 and an array of a plurality of photodiodes 2.3.4, e. g. each comprising silicon material, could be advantageous due to the fact that infrared radiation emitting diodes 2.2.5 are powerful, economical and durable at least until a wavelength range of 900 nm and that photodiodes 2.3.4 comprising silicon are cost-effective and comprise peak sensitivity at a wavelength range of 905 nm, which is close to the peak wavelength emission spectrum of the infrared radiation emitting diode 2.2.5.

Following, an exemplary configuration of the infrared readable data D provided on the movable component 1.1 according to FIGS. 1 and 2 will be described in more detail.

Figure 3:
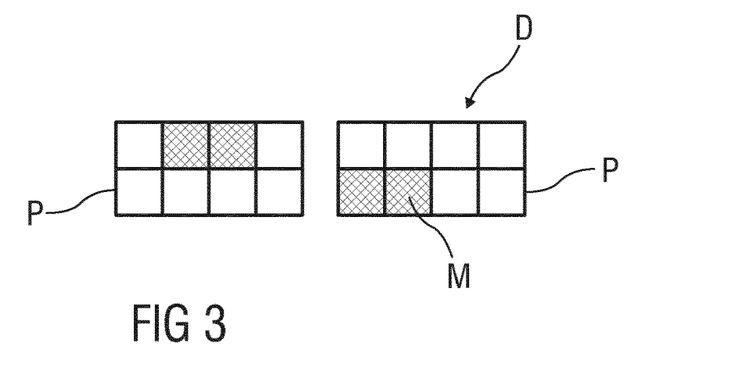
FIG. 3 is a schematic view of two pixel patterns each comprising two rows of four pixel and a machine or infrared readable data represented by a binary code, according to the embodiments of the present disclosure.

FIG. 3 shows two exemplary embodiments of a pixel pattern P comprising two rows of four pixels that result in a sum of eight pixels. By reference to the so-called Nyquist-Shannon sampling theorem, at least two pixels of the pixel pattern P are required to be filled with metal, thereby generating a specific binary code i, depending on which pixels are filled.

Figure 4:
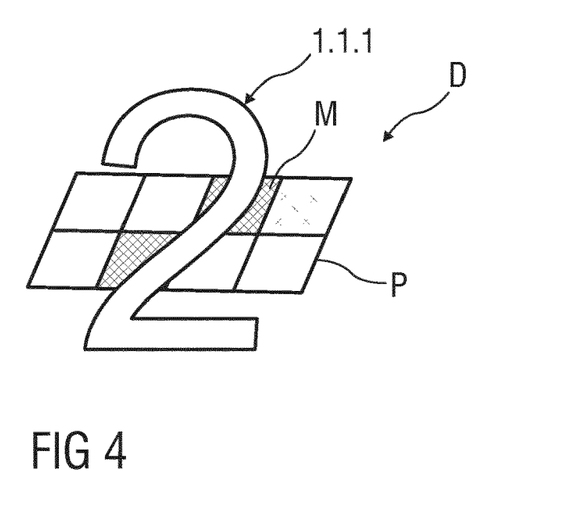
FIG. 4 is a schematic view of a visual data represented by a single digit of a number and an infrared readable data assigned to the visual data, according to the embodiments of the present disclosure.

FIG. 4 schematically shows a single visual symbol 1.1.1, here "2", and an infrared readable symbol $D_{ir}$ assigned to this visual symbol 1.1.1.

Generally, every digit of the visual symbols 1.1.1 is dedicated to a specific binary code, which results in sum to a sequence of binary codes forming infrared readable symbol $D_{ir}$, which is assigned to the specific visual symbol 1.1.1. Here, the visual symbol 1.1.1 "2" is printed above the infrared readable symbol $D_{ir}$, whereby the layer between the visual symbol 1.1.1 and the infrared readable symbol $D_{ir}$ is not shown.

Figure 5:
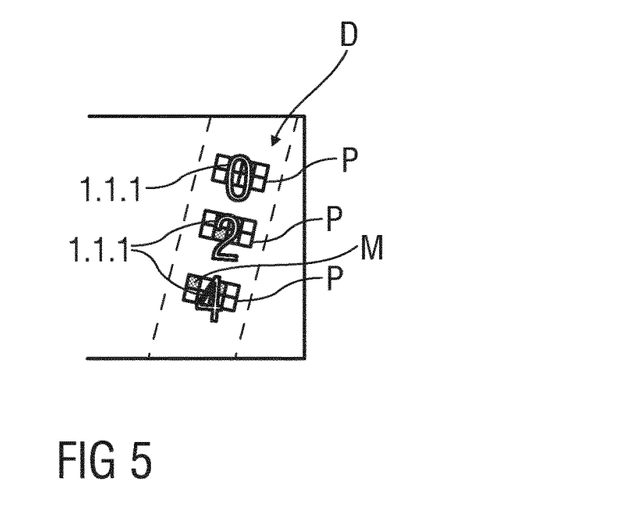
FIG. 5 is a schematic view of a visual data represented by three digits and an assigned infrared readable data, according to the embodiments of the present disclosure.

FIG. 5 illustrates a visual symbol 1.1.1 printed as "024" and thus comprising the digits "0", "2", and "4" in sequence. The digit "0" may be associated to a binary code represented by only one filled pixel. The digits "2" and "4" are associated to a binary code respectively represented by two different filled pixels. The binary codes result in sum to the specific infrared readable symbol $D_{ir}$ that is associated to the visual symbol 1.1.1 printed as "024".

Figure 6:
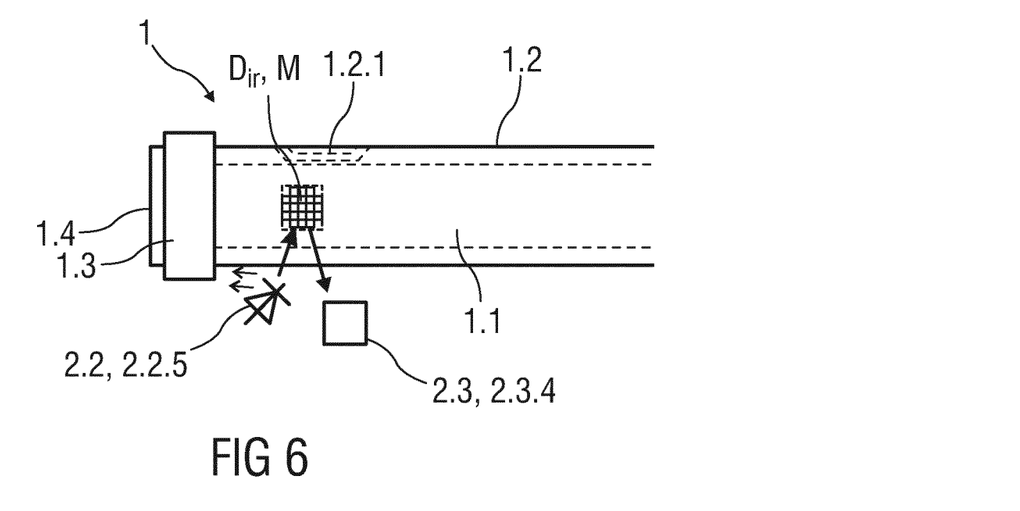
FIG. 6 is a schematic perspective view of a cut-out of an exemplary embodiment of a drug delivery device and a reading device, according to the embodiments of the present disclosure.

FIG. 6 shows a schematic cut out of the exemplary embodiment of the drug delivery device 1 similar to that shown in FIGS. 1 and 2.

The window 1.2.1 and the electromagnetic radiation source 2.2 are arranged opposite to each other in a circumferential direction, whereby the optical sensor unit 2.3 is arranged adjacent to the electromagnetic radiation source 2.2 in order to receive reflected electromagnetic radiation and converting the reflected electromagnetic radiation into an image. For example, the window 1.2.1 is facing a patient and the electromagnetic radiation source 2.2 and the optical sensor unit 2.3 are arranged on the opposite side. That means the optical sensor unit 2.3 detects electromagnetic radiation reflected from an infrared readable symbol $D_{ir}$ that is covered by a layer on which the visual symbol 1.1.1 is arranged that is currently not indicated through the window 1.2.1 and being thus offset to the visual symbol 1.1.1, which is currently aligned with the window 1.2.1.

The visual symbol 1.1.1 that is currently visible through the window 1.2.1 and the assigned infrared readable symbol $D_{ir}$ are arranged offset to each other at a certain angle, e.g., at an angle of 180 degrees, in a plane that is perpendicular to a longitudinal axis of the drug delivery device 1. This must be taken into account when evaluating the reflected electromagnetic radiation as it is described in context with FIG. 10.

Figure 7:
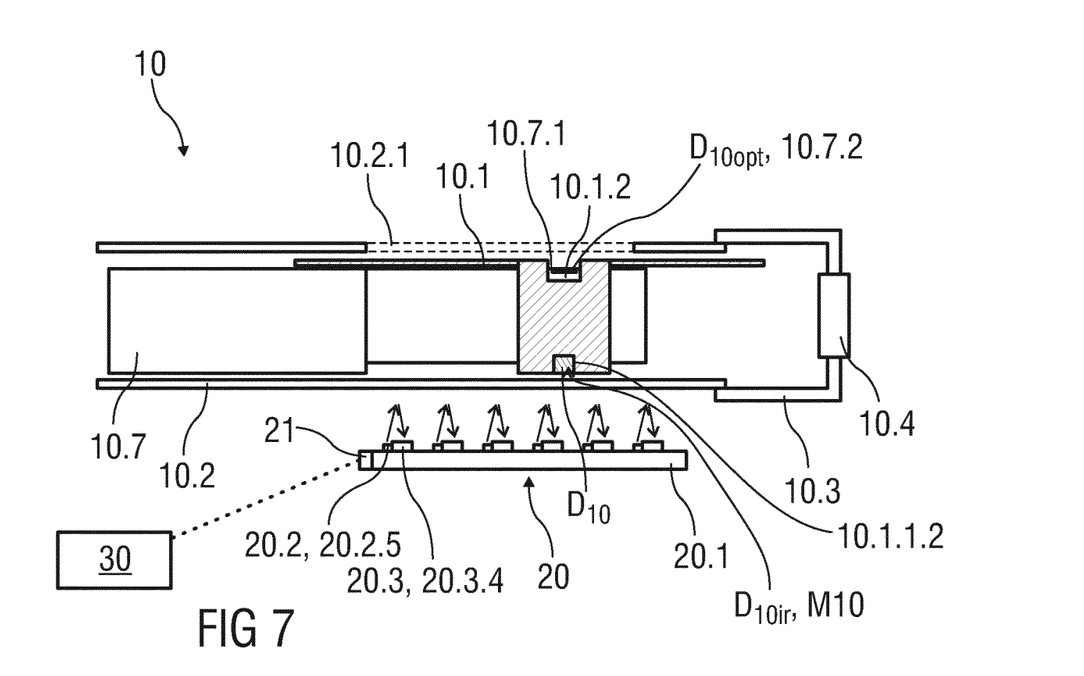
FIG. 7 is a schematic cut-out view of a cut-out of an alternative exemplary embodiment of the drug delivery device and the reading device, according to the embodiments of the present disclosure.

FIG. 7 shows a schematic cut-out view of an alternative exemplary embodiment of a drug delivery device 10 and a reading device 20.

The drug delivery device 10 may be configured as a pre-filled, disposable injection pen or as an autoinjector comprising a case 10.2 receiving a movable component 10.1 and at least a medicament container 10.5 (see FIG. 10) to which a needle may be fixed (not illustrated). The needle may be protected by an inner needle cap and an outer needle cap (not illustrated).

A dose of medicament to be ejected from the drug delivery device 10 can be selected by turning a dose selector 10.3, e. g. a dial grip, in a rotational direction. The dose selector 10.3 is coupled to a dose indicator sleeve 10.7 in a manner such that the dose indicator sleeve 10.7 rotates together with the dose selector 10.3. The dose indicator sleeve 10.7 is provided with visual data $D_{10opt}$, which is represented by a sequence of visual symbols 10.7.1. The visual symbols 10.7.1. are printed or laser marked spirally around a part 10.7.2 of the dose indicator sleeve 10.7, wherein the part 10.7.2 of the dose indicator sleeve 10.7 is an outer circumference of the dose indicator sleeve 10.7.

According to the present embodiment, the movable component 10.1 is configured as a gauge element that may have the shape of a shield or a strip extending in a longitudinal direction of the drug delivery device 10. As an alternative, the movable component 10.1 may be a sleeve.

The movable component 10.1 is arranged between the case 10.2 and the dose indicator sleeve 10.7 and is partly visible through a window 10.2.1 arranged within the case 10.2. The window 10.2.1 is a transparent or light permeable part of the case 10.2 that may have larger dimensions than the window 1.2.1 illustrated in FIG. 1. In particular, the window 1.2.1 extends in a longitudinal direction enabling to indicate a longitudinal portion of the dose indicator sleeve 10.7.

For indicating the currently set or remaining dose of medicament, the movable component 10.1 comprises a gauge window 10.1.2 that is arranged with respect to the window 10.2.1 such that a part of the dose indicator sleeve 10.7, in particular the currently set or remaining dose of medicament, is visible through the window 10.2.1 and the gauge window 10.1.2. In other words, the movable component 10.1 may be used to shield or cover a portion of the dose indicator sleeve 10.7 and to allow viewing only on a limited portion of the dose indicator sleeve 10.7 that indicates the currently set and/or dispensed dose of medicament.

To facilitate this, the dose indicator sleeve 10.7 and the movable component 10.1 may be in a threaded engagement such that the movable component 10.1 is axially displaced with respect to the case 10.2 and the dose indicator sleeve 10.7 upon rotation of the dose indicator sleeve 10.7. That means, as the dose selector 10.3 is dialled, the dose indicators sleeve 10.7 rotates correspondingly and the movable component 10.1 moves axially along the outer circumference of the dose indicator sleeve 10.7.

Furthermore, the movable component 10.1 is provided with infrared readable data $D_{10}$ that may be represented by an infrared readable symbol $D_{10ir}$, which is configured as a metal area M10 printed on a covered part 10.1.1.2 of the movable component 10.1, wherein the covered part 10.1.1.2 is an outer section of the movable component 10.1 that is covered by an opaque part of the case 10.2. The infrared readable data $D_{10}$ is used to detect an axial position of the movable component 10.1 with respect to the dose indicator sleeve 10.7 in order to determine the currently set or remaining dose of medicament, which is visibly indicated through the gauge window 10.1.2. According to the present embodiment, the infrared readable symbol $D_{10ir}$ is arranged on a side of the movable component that is opposite to the gauge window 10.1.2 in a circumferential direction.

The detection of the axial position of the movable component 10.1 with respect to the dose indicator sleeve 10.7 is carried out by the reading device 20.

The reading device 20 is a supplemental component to the drug delivery device 10. In particular, the reading device 20 may be configured to be attached to the drug delivery device 10, for example releasably or alternatively irreleasably. Alternatively, the reading device 20 is configured as a remote component.

The reading device 20 may optionally comprise a transmitter 21 to transmit the data and/or the data value as read from the drug delivery device 10 to another device 30, e.g. transmit the data wirelessly, for example via radio, to a mobile phone or a walk-by device or a remote terminal.

The reading device 20 comprises an array of six electromagnetic radiation sources 20.2 and six corresponding photodiodes 20.3.4 forming the optical sensor unit 20.3. The optical sensor unit 20.3 is configured to detect an axial position of the infrared readable symbol $D_{10ir}$ that is provided on the covered part 10.1.1.2 of the movable component 10.1. The number of electromagnetic radiation sources 20.2 and corresponding photodiodes 20.3.4 is exemplarily used because it may be required to recognize only six different axial positions of the movable component 10.1 in order to evaluate the currently set or remaining dose of medicament. For example, this may be due to a total amount of possible doses of medicament of 120 International Units that are helically distributed about the outer circumference of the dose indicator sleeve 10.7 over five turns. The number of electromagnetic radiation sources 20.2 and corresponding photodiodes 20.3.4 is thus suitable to detect the five turns in the longitudinal direction.

The reading device 20 may be coupled to the drug delivery device 10 by connecting a housing 20.1 of the reading device 20 with the case 10.2 of the drug delivery device 10, e.g., by one or more protrusions and/or one or more indentations as mentioned above. In particular, the reading device 20 may be coupled adjacent to the window 10.2.1 in order not to cover the window 10.2.1 and the gauge window 10.1.2, thereby facing an angular portion of the movable component 10.1 that comprises the covered part 10.1.1.2 on which the infrared readable symbol $D_{10ir}$ is arranged.

Furthermore, the reading device 20 may be coupled to the drug delivery device 10 such that the array of six electromagnetic radiation sources 20.2 and six corresponding photodiodes 20.3.4 extends along an axis that is substantially parallel to the axis along which the movable component 10.1 is configured to move. A longitudinal extension of the reading device 20 may be nearly similar to a longitudinal extension of the window 10.2.1. In particular, one end-side electromagnetic radiation source 20.2 is located above one end of the window 10.2.1 at which the gauge window 10.1.2 is located when the minimum dose is set. An opposite end-side electromagnetic radiation source 20.2 is located above the other end of the window 10.2.1 at which the gauge window 10.1.2 is located when the maximum dose is set.

The case 10.2 and the movable component 10.1 may be illuminated by the electromagnetic radiation sources 20.2 by successively generating short and high current pulses through the electromagnetic radiation sources 20.2, which may emit low-frequency infrared radiation. This enables to successively query signal responses of the photodiodes 20.3.4, whereby one of the photodiodes 20.3.4 detects reflected infrared radiation when the emitted infrared radiation strikes the metal area M10 on the movable component 10.1. By means of predetermined angular position information of the electromagnetic radiation sources 2.2 and/or the corresponding photodiodes 20.3.4 with respect to the gauge window 10.1.2., an absolute value of the currently set dose indicated through the gauge window 10.1.2 can be evaluated.

FIG. 8 shows a circuit diagram of a single electromagnetic radiation source 20.2 of the reading device 20 according to the exemplary embodiment illustrated in FIG. 7. The electromagnetic radiation source 20.2 is configured as an electromagnetic radiation emitting diode 20.2.5. The circuit diagram shows a power source 20.2.1, e.g., a current source, a diode 20.2.2, a resistor 20.2.3 and a transistor 20.2.4. The transistor 20.2.4 is connected to the diode 20.2.2, which is coupled to the power source 20.2.1 in a forward conducting direction. The resistor 20.2.3 is arranged between the diode 20.2.2 and the transistor 20.2.4.

The power source 20.2.1 provides short but high current pulses for a powerful and efficiency operation of the electromagnetic radiation source 20.2.

Figure 9:
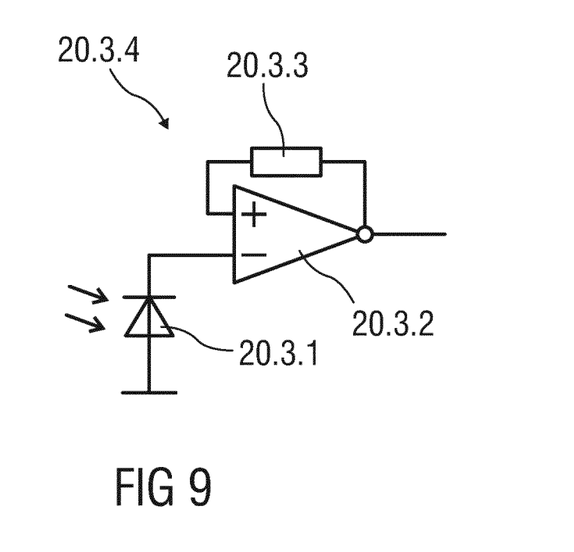
FIG. 9 is a circuit diagram of an optical sensor unit of a reading device, according to the embodiments of the present disclosure.

FIG. 9 shows a circuit diagram of a single photodiode 20.3.4 of an optical sensor unit 20.3 according to the exemplary embodiment illustrated in FIG. 7.

The circuit diagram shows a further diode 20.3.1, e.g., an electromagnetic radiation sensitive photodiode, coupled to a comparator 20.3.2 that is coupled with a further resistor 20.3.3 in turn.

As mentioned above, the optical sensor unit 20.3 is adapted to receive reflected infrared light. The intensity of the reflected infrared light depends on the configuration of the metal area and thus on the specific binary code. For decoding the data $D_{10}$ by analysing the reflected electromagnetic radiation detected from the further diode 20.3.1, the optical sensor unit 20.3 is coupled to a processing unit 20.4 as illustrated in FIG. 10.

Figure 10:
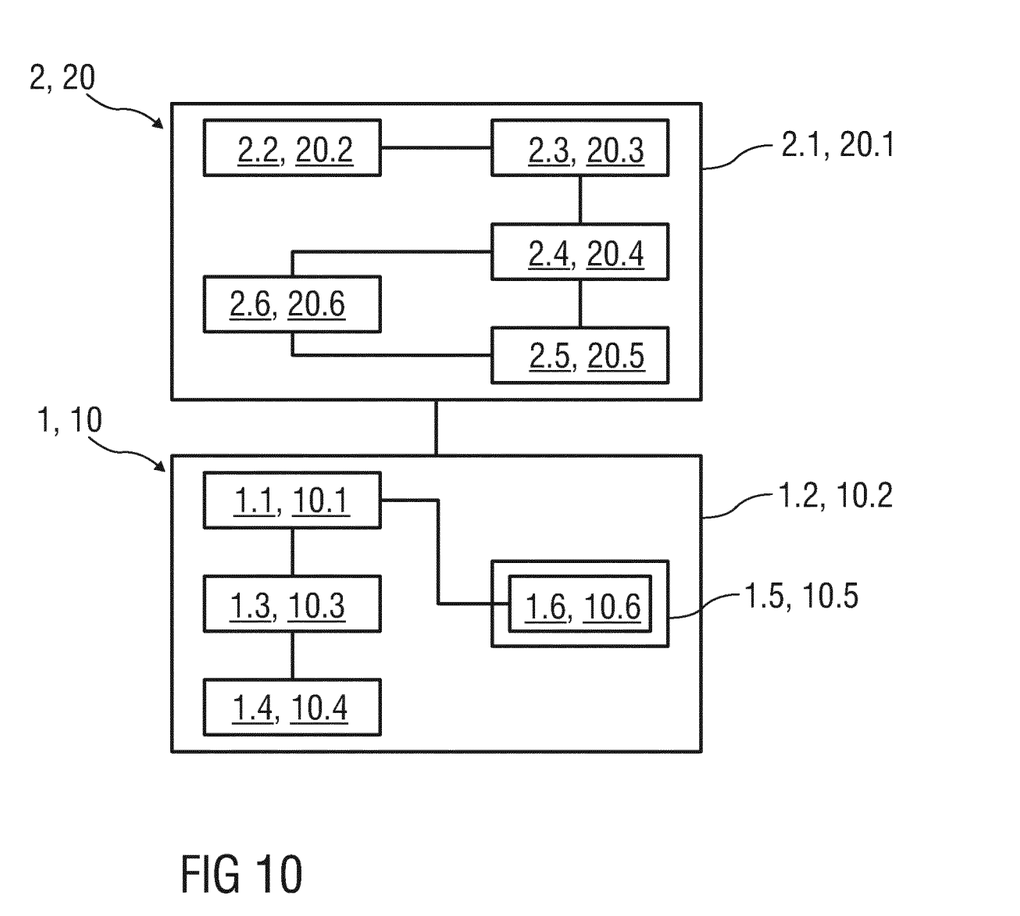
FIG. 10 is a block diagram representing a reading device and a drug delivery device, according to the embodiments of the present disclosure.

FIG. 10 is a block diagram of the reading device 2, 20 and the drug delivery device 1, 10. The reading device 2, 20 comprises the housing 2.1, 20.1, the electromagnetic radiation source 2.2 or electromagnetic radiation sources 20.2, the optical sensor unit 2.3, 20.3, the processing unit 2.4, 20.4, a memory unit 2.5, 20.5 and a display unit 2.6, 20.6.

The processing unit 2.4, 20.4 may be configured as a microprocessor received within the housing 2.1, 20.1. The processing unit 2.4, 20.4 is coupled to the optical sensor unit

2.3, 20.3 for decoding the infrared readable data D, $D_{10}$ in order to evaluate which dose is currently selected. Because the reading device 2, 20 is arranged such that the window 1.2.1, 10.2.1 is not covered, the optical sensor unit 2.3, 20.3 receives electromagnetic radiation reflected from the infrared readable symbols $D_{ir}$, $D_{10ir}$ that is located offset to the window 1.2.1, 10.2.1, 10.1.2 at a certain angle, e. g. at an angle of 180 degrees. The detail information regarding a position of the electromagnetic radiation source 2.2 or the electromagnetic radiation sources 20.2 with respect to the window 1.2.1, 10.2.1 may be saved in the processing unit 2.4, 20.4.

Referring to the exemplary embodiment of the drug delivery device 10 illustrated in FIG. 7, the electromagnetic radiation sources 20.2 will be subjected to short and high current pulses, whereby one of the photodiodes of the optical sensor unit 20.3 detects reflected electromagnetic radiation. This has the advantage that other disturbing effects, e. g. extraneous electromagnetic radiation, will be faded. Furthermore, the evaluation of the currently set or remaining dose of medicament indicated through the gauge window 10.1.2 may be performed in an easy manner, e.g., by thresholding (image processing).

Alternatively, the optical sensor unit 20.3 may be analysed by use of a constant pulse period, e.g., by pulse width modulation of the reflected electromagnetic radiation signal at 50% or by pulse width modulation of the electromagnetic radiation signal emitted by the electromagnetic radiation sources 20.2.

In further alternative embodiments, the processing unit 20.4 may be provided with or coupled to a so-called lock-in amplifier comprising a multiplier or to a pseudo-random signal generator. The latter includes detecting reflected electromagnetic radiation by the optical sensor unit 20.3 over a measurement period having several light-dark phases that may be integrated over the measurement period, thereby forming an irregular sequence such that a Fourier-transformed frequency spectrum includes a plurality of different frequencies. Each individual frequency makes only a small contribution to the measurement result. This allows for a high signal-to-noise ratio.

By starting or activating the reading device 20, the row of electromagnetic radiation sources 20.2 will be successively queried as it is described already in context with FIG. 7. It is required to detect exactly one reflected electromagnetic radiation signal. If no reflected electromagnetic radiation signal or more than one reflected electromagnetic radiation signals are detected, an error has occurred. At the beginning of a dose selection performance, the reflected electromagnetic radiation signal is detected by a predetermined first photodiode of the optical sensor unit 20.3. Otherwise, the drug delivery device 10 is not set to zero. For this purpose, the reading device 10 is calibrated to a predetermined standard signal.

During dose selection, the reflected signal changes, i.e., the dose indicator sleeve 10.7, rotates and the movable component 10.1 moves axially with respect to the dose indicator sleeve 10.7. It may be then concluded that the visual symbol 10.7.1 that is currently indicated through the gauge window 10.2.1 has changed. Current positions of the movable component 10.1 relative to the reading device 20 are clearly identifiable, because intermediate areas between the photodiodes 20.3.4 supply two signals smaller than one signal of a center area.

If no more changes occur, it can be assumed that dose setting is finished. Then the evaluated value of the dialled dose will be saved. When the patient starts an injection process, the movable component 1.1 rotates in the other direction or the movable component 10.1 moves in the other axial direction and the visual symbols 1.1.1, 10.7.1, i.e., the set dose, count to zero. If the current dose comprises the value "0", thereby assuming that injection had really occurred, the value of the dose set before may be saved in the memory unit 2.5, 20.5. Preferably, the memory unit 2.5, 20.5 is configured to store a plurality of history values. The current and/or history values may be visually indicated via the display unit 2.6, 20.6. Alternatively or additionally, the current and/or history values may be acoustically indicated.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin; B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine. Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

LIST OF REFERENCES 1, 10 drug delivery device
1.1, 10.1 movable component
1.1.1 visual symbol
1.1.1.1 visible part
1.1.1.2 covered part
10.1.1.2 covered part
10.1.2 gauge window
1.2, 10.2 case
1.2.1, 10.2.1 window
1.3, 10.3 dose selector
1.4, 10.4 button
1.5, 10.5 medicament container
1.6, 10.6 piston
10.7 dose indicator sleeve
10.7.1 visual symbol
10.7.2 visible part
2, 20 reading device
2.1, 20.1 housing
2.2, 20.2 electromagnetic radiation source
20.2.1 power source
20.2.2 diode
20.2.3 resistor
20.2.4 transistor
2.2.5, 20.2.5 electromagnetic radiation emitting diode
2.3, 20.3 optical sensor unit
20.3.1 diode
20.3.2 comparator
20.3.3 resistor
2.3.4, 20.3.4 photodiode
2.4, 20.4 processing unit
2.5, 20.5 memory unit
2.6, 20.6 display unit
transmitter
device
$D$, $D_{10}$ infrared readable data
$D_{ir}$, $D_{10ir}$ infrared readable symbol
$D_{opt}$, $D_{10opt}$ visual data
M, M10 metal area
P pixel pattern

The invention claimed is:

1. A drug delivery device adapted to dispense a variable dose of a medicament and to couple to a reading device, the drug delivery device comprising:
a case; and
at least one movable component arranged within and movable with respect to the case, the at least one movable component having a covered part that provides infrared readable representations of data, wherein the covered part of the at least one movable component is covered by an opaque outer surface of the at least one movable component, wherein a first movable component of the at least one movable component is configured to allow visual representations of data assigned to the infrared readable representations of data to be viewed by a user, wherein the visual representations of data are each associated with a respective infrared readable representation of data of the infrared readable representations of data,
wherein the reading device is adapted to read-out the infrared readable representations of data through the case.

2. The drug delivery device according to claim 1, wherein the infrared readable representations of data are represented by at least one of infrared readable symbols, signs, characters, icons, markings, codes, or signals arranged on the covered part.

3. The drug delivery device according to claim 1, wherein the visual representations of data are represented by at least one of visual symbols, signs, characters, icons, markings, or signals arranged on the first movable component.

4. The drug delivery device according to claim 1, wherein the infrared readable representations of data and the visual representations of data are assigned to the same data values characterizing at least one of a parameter, a state, a dose and a position of at least one of a medicament, a component of the drug delivery device, or the drug delivery device.

5. The drug delivery device according to claim 1, wherein the infrared readable representations of data are represented by a number of metal areas printed on the covered part.

6. The drug delivery device according to claim 1, wherein the visual representations of data are arranged on the opaque outer surface such that the visual representations of data are visible through a window, and
the window is arranged within the case such that the visual representations of data are visible through the window.

7. The drug delivery device according to claim 6, wherein the at least one movable component is configured as a number sleeve, whereby the number sleeve is rotatable with respect to the case.

8. The drug delivery device according to claim 1, wherein the infrared readable representations of data are arranged on the covered part of the at least one movable component such that visual representations of data are arranged phase-shifted to the infrared readable representations of data.

9. The drug delivery device according to claim 1, whereby the at least one movable component is axially movable with respect to the case.

10. The drug delivery device according to claim 1, wherein the visual representations of data each are associated with a respective infrared readable representation of data of the infrared readable representations of data based on a respective binary code.

11. A drug delivery device in combination with a reading device, wherein the drug delivery device comprises:
   a case; and
   at least one movable component arranged within and movable with respect to the case, the at least one movable component having a covered part that provides infrared readable representations of data, wherein the covered part of the at least one movable component is covered by an opaque outer surface of the at least one movable component, wherein a first movable component of the at least one movable component is configured to allow visual representations of data assigned to the infrared readable representations of data to be viewed by a user, wherein the visual representations of data are each associated with a respective infrared readable representation of data of the infrared readable representations of data,
   wherein the reading device is adapted to read-out the infrared readable representations of data through the case.

12. The drug delivery device in combination with a reading device according to claim 11, wherein the reading device comprises:
   at least one electromagnetic radiation source configured to emit electromagnetic radiation and adapted to illuminate the covered part of the at least one movable component;
   at least one optical sensor unit configured to detect electromagnetic radiation reflected from the at least one movable component; and
   at least one processing unit configured to determine a data value of the infrared readable representations of data as a function of the detected reflected electromagnetic radiation.

13. The drug delivery device in combination with the reading device according to claim 12, wherein the at least one electromagnetic radiation source is configured to emit infrared radiation.

* * * * *